United States Patent
Ripamonti et al.

(10) Patent No.: US 6,302,913 B1
(45) Date of Patent: *Oct. 16, 2001

(54) BIOMATERIAL AND BONE IMPLANT FOR BONE REPAIR AND REPLACEMENT

(75) Inventors: Ugo Ripamonti, Killarney; Anthony Nigel Kirkbride, Moreleta Park, both of (ZA)

(73) Assignee: Implico B.V., Amsterdam (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/737,760

(22) PCT Filed: May 24, 1995

(86) PCT No.: PCT/NL95/00181

§ 371 Date: Nov. 22, 1996

§ 102(e) Date: Nov. 22, 1996

(87) PCT Pub. No.: WO95/32008

PCT Pub. Date: Nov. 30, 1995

(30) Foreign Application Priority Data

May 24, 1994 (ZA) .................................................. 94/3608
Dec. 21, 1994 (ZA) .................................................. 94/10206

(51) Int. Cl.[7] ....................................................... A61F 2/28
(52) U.S. Cl. .................. 623/16.11; 623/23.3; 623/23.56; 623/23.76
(58) Field of Search .................................. 623/16, 18, 66

(56) References Cited

U.S. PATENT DOCUMENTS

| | | | |
|---|---|---|---|
| 4,070,514 | * | 1/1978 | Eatherly et al. ................... 623/16 |
| 4,156,943 | * | 6/1979 | Collier ............................... 623/16 |
| 4,309,488 | * | 1/1982 | Heide et al. ........................ 623/16 |
| 4,330,891 | * | 5/1982 | Branemark et al. ................ 623/16 |

(List continued on next page.)

FOREIGN PATENT DOCUMENTS

| | | |
|---|---|---|
| 42 11 343 A1 | 10/1993 | (DE) . |
| 0 267 624 | 5/1988 | (EP) . |
| 0 475 358 | 3/1992 | (EP) . |

(List continued on next page.)

OTHER PUBLICATIONS

Lynch et al., "Osteoinductivity by Subcutaneous Implant of a Collagen/Ceramic Composite", 3rd International Symposium on Ceramics in Medicine, Abstracts (Nov. 18–20, 1990).

Piecuch article entitled "Extraskeletal Implantation of a Porous Hydroxyapatite Ceramic", Journal of Dental Research, Dec. 1982, pp. 1458–1460.

Wells JW, (1956) Scleractinia. In: Moore RC (ed) Treaties on Invertebrate Paleontology, University of Kansas Press, Kansas City, pp. F328–F443.

Weber JN White EW (1973) Carbonate minerals as precursors of new ceramics, metal, and polymer materials for biomedical applications. Miner Sci Engng., vol. 5, No. 2, Apr. 1975, pp. 151–165.

(List continued on next page.)

Primary Examiner—Michael J. Milano
Assistant Examiner—Choon P. Koh
(74) Attorney, Agent, or Firm—Frommer Lawrence & Haug, LLP.; William S. Frommer

(57) ABSTRACT

This invention relates to a biomaterial useful in bone repair and replacement, and to implants for cranofacial, orthopaedic, and especially dental applications. The implants have a unique geometric configuration, their surfaces defining concavities having a shape and dimensions which induce or enhance the rate and/or amount of bone growth at the implant site. The biomaterial preferably has a specific porous configuration and the implant may be at least coated with such a biomaterial of hydroxyapatite, for example.

7 Claims, 18 Drawing Sheets

U.S. PATENT DOCUMENTS

Figure 1:
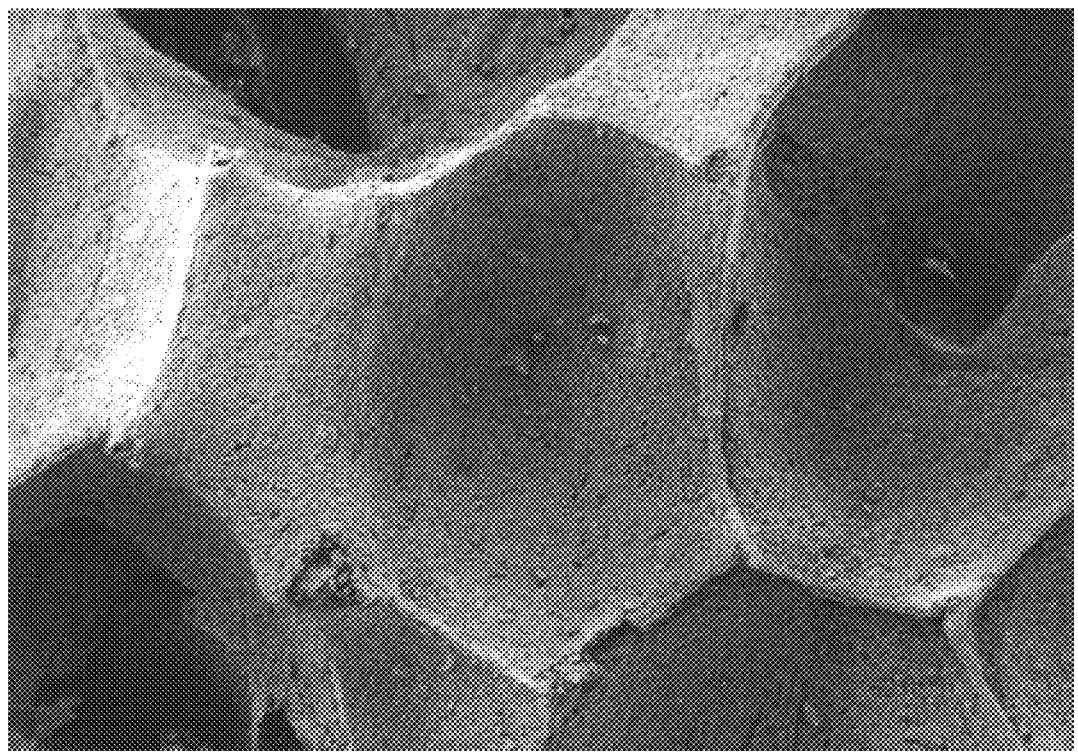

| | | | |
|---|---|---|---|
| 4,366,183 | * | 12/1982 | Ghommidh et al. .................... 623/16 |
| 4,492,577 | | 1/1985 | Farris et al. . |
| 4,608,052 | * | 8/1986 | Van Kampen et al. ............... 623/16 |
| 4,629,464 | | 12/1986 | Takata et al. . |
| 4,654,314 | | 3/1987 | Takagi et al. . |
| 4,780,450 | | 10/1988 | Sauk et al. . |
| 4,794,046 | | 12/1988 | Nagai . |
| 4,795,467 | | 1/1989 | Piez et al. . |
| 4,795,472 | * | 1/1989 | Crownfield et al. .................... 623/16 |
| 4,932,973 | | 6/1990 | Gendler et al. . |
| 5,171,327 | | 12/1992 | Koch et al. . |
| 5,236,456 | * | 8/1993 | O'Leary et al. ........................ 623/16 |
| 5,282,861 | * | 2/1994 | Kaplan .................................. 623/16 |
| 5,306,303 | | 4/1994 | Lynch . |
| 5,355,898 | | 10/1994 | Ripamonti . |

FOREIGN PATENT DOCUMENTS

| | | |
|---|---|---|
| 2 548 661 | 1/1985 | (FR) . |
| WO 87/07495 | 12/1987 | (WO) . |
| WO 94/28827 | 12/1994 | (WO) . |
| 93/6411 | 8/1993 | (ZA) . |

OTHER PUBLICATIONS

Roy DM, Linnehan SK (1974), Hydroxyapatite formed from coral skeletal carbonate by hydrothermal exchange. Nature 247:220–222.

White EW, Weber JN, Roy DM, Owen EL (1975) Replamineform porous biomaterials for hard tissue implant applications. J Biomed Mater Res Symposium 6:23–27.

Ripamonti U. The morphogenesis of bone in replicas of porous hydroxyapatite obtained from conversion of calcium carbonate exoskeletons of coral. J Bone joint Surg (Am) 1991; 73:692–703.

Ripamonti U, Ma S, Reddi AH. The critical role of geometry of porous hydroxyapatite delivery system in induction of bone by osteogenin, a bone morphogenetic protein, Matrix 1992; 12:202–212.

Ripamonti U, Van der Heever B, Van Wyk J. Expression of the osteogenic phenotype in porous hydroxyapatite implanted extraskeletally in baboons. Matrix 1993; 13:491–502.

Van Eeden S, Ripamonti U. Bone differentiation in porous hydroxyapatite is regulated by the geometry of the substratum: implications for reconstructive craniofacial surgery. Plast Reconstr Surg 1994; 959–966.

Schnitzler CM, Ripamonti U, Mesquita JM. Histomorphometry of iliac crest trabecular bone in adult male baboons in captivity, Calcif Tiss Int 1993; 52:447–454.

Ripamonti U, Inductive Bone Matrix and Porous Hydroxylapatite Composites in Rodents and Non–Human Primates, CRC Handbook of Bioactive Ceramics, vol. II, pp. 245–253.

Yamasaki H, Sakai H, "Osteogenic Response to Porous Hydroxyapatite Ceramics under the Skin of the Dog", Biomaterials 1992; 13; pp. 308–312.

Vargervik K, "Critical Sites for New Bone Formation", Bone Graftsand Bone Substitutes, Habal MB, Reddi AH (Eds), WB Saunders, 1992, pp. 112–120; and.

Toth JM, Lynch KL, Hackbarth DA, "Ceramic–Induced Osteogenesis following Subcutaneous Implantation of Calcium Phosphates", Bioceramics, vol. 3, 1993, pp. 9–14.

* cited by examiner-

BIOMATERIAL AND BONE IMPLANT FOR BONE REPAIR AND REPLACEMENT

This invention relates to a biomaterial useful in bone repair and replacement, and to implants for craniofacial, orthopaedic, and especially dental applications.

Successful osteointegration of implants for dental, craniofacial and orthopaedic applications is a problem central to oral and skeletal rehabilitation.

Conventional treatment of bone defects require the use of either organic (bone derived) or inorganic (man made) biomaterials for successful restoration of form and function, preferably biomaterials with interconnected porous spaces across the substratum of the biomaterial. This allows bone growth into the porous spaces of the biomaterial, securing its incorporation and osteointegration with the surrounding viable bone at the margins of the bone defect. Porous biomaterials which allow bone growth thus into their porous spaces are defined as osteoconductive biomaterials.

The necessity of having viable bone in direct contact with the porous biomaterial to ensure adequate bone ingrowth via osteoconduction is, however, a limiting factor particularly in large bony defects, since the depth of bone penetration within the porous spaces may be confined to the peripheral regions of the implant only. Furthermore, a perfect fit of an implant, designed for orthopaedic and dental applications either for bone repair or replacement, within a bone defect is often technically difficult to achieve, since it is not always possible to prepare the bone margins precisely so as to provide a perfect fit to the implants. Thus, in spite of technological advances in implant design and fabrication, osteointegration often doe not occur or is not maintained along the entire implant surface.

Thus for several applications, it would be preferred for bone to grow more rapidly into the porous spaces and, further, for bone to form independently of the surrounding viable bone, within the biomaterial. The formation of bone within a porous biomaterial independent of the presence of viable bone (when for example the biomaterial is implanted in extraskeletal sites) is defined as osteoinduction. One approach for preparing an osteoinductive material is to adsorb onto its surfaces exogenous growth and morphogenetic factors which are capable of inducing differentiation of bone within the porous spaces of the biomaterial. These molecular initiators of bone formation are collectively named bone morphogenetic proteins (BMPs).

This, however, requires the complexing, onto the biomaterial, of either native BMPs (isolated and purified from organic bone matrix—in particular bovine bone) or recombinant human BMPs, with the accompanying disadvantages of a limited shelf life and possible adverse systemic effects. A preferred alternative would be a biomaterial which is capable of spontaneously initiating bone formation within the porous spaces independent of the presence of viable bone at its interfaces.

The Applicant is aware of previous studies involving the calcium phosphate ceramic called hydroxyapatite [$Ca_{10}(PO_4)_6(OH)_2$] obtained after hydrothermal chemical exchange with phosphate converting the original calcium carbonate exoskeletal microstructure of the scleractinian reef-building coral of the genus Goniopora [1] into an inorganic replica of hydroxyapatite [2–4]. Conversion to hydroxyapatite is monitored by X-ray diffraction pattern, showing that hydroxyapatite replicas consist of ±90% hydroxyapatite and 10% tricalcium phosphate. Previous studies by one of the inventors, Dr Ripamonti, using coral-derived hydroxyapatite introduced the concept that the shape and configuration (hereinafter referred to as "the geometry") of the hydroxyapatite implant regulate the initiation of bone formation in vivo [6]. These studies showed that in extraskeletal sites of rodents, bone did not form in implants of granular hydroxyapatite, even when pre-treated with bone morphogenetic proteins (BMPs) (which initiate bone differentiation in vivo), while bone formation was observed in porous blocks of hydroxyapatite [5–8]. As part of the research into the subject of spontaneous bone growth and, in particular, the optimum conditions for initiating bone growth, extraskeletal implantation of different forms of hydroxyapatite into primates indicated that the geometry of the hydroxyapatite indeed is important and indeed might even be critical for bone induction to occur [5,7,8]. When implanted intramuscularly in baboons, granular hydroxyapatite implants did not induce the differentiation of bone, while reproducible bone differentiation was observed in porous blocks of hydroxyapatite with identical surface characteristics [5,7,8].

Thus it appeared from said inventor's studies that a critical difference between geometries is the presence of convexities in granular hydroxyapatite and, conversely, the presence of concavities (of the porous space) in the blocks of hydroxyapatite.

Accordingly it is an object of this invention to provide implants for bone repair and bone replacement having a defined macrostructure and especially a defined geometric configuration of the implant surface, i.e. implants with geometric osteoinductive configurations.

It is another object of this invention to provide a biomaterial for bone replacement which is capable of spontaneous initiation of bone formation, i.e. a biomaterial with intrinsic osteoinductive activity.

It is another object of this invention to provide sintered porous ceramic biomaterials and methods for their manufacture derived from synthetic hydroxyapatite particles as starting material.

It is a further object of this invention to provide sintered ceramic biomaterials capable of osteoconduction when implanted into a bone defect.

It is a further object of this invention to provide sintered porous ceramic biomaterials for bone replacement having a defined porous macrostructure and especially a defined geometric configuration of the porous structure (osteoinductive configuration).

It is a further object of this invention to enhance the extent of bone formation and/or bone growth by pre-treatment of the porous sintered hydroxyapatite with liquid etchants.

It is yet a further object of this invention to provide porous sintered ceramic biomaterials which provide an optimal substratum for adsorption of growth and morphogenetic factors, including, but not limited to BMPs.

It is a still further object of this invention to provide a composite of porous ceramic and native or recombinant human BMPs for the rapid initiation of bone formation within the porous spaces of the implant.

A further, important object of this invention is to provide a bone implant for orthopaedic, craniofacial, and particularly dental applications.

How the objectives of this invention are achieved will become apparent in the light of the following disclosure.

Whilst restoration of bone defects may be sought by insertion at the site of the bone defect of porous osteoconductive biomaterials or implants, in several instance treatment requires the insertion of solid prostheses that substitute for a part of the skeleton, as commonly done for femoral and knee replacement (for example, hip and knee prosthesis).

Similarly, dental implants (usually of titanium with or without hydroxyapatite coating) are used as surrogates of tooth roots after implantation in edentulous jaws. Both porous biomaterial implants and solid prosthetic implants for orthopaedic, craniofacial and dental applications need to integrate with the host viable bone for successful osteointegration. It is common knowledge that osteointegration may not occur or is not maintained along the entire surface of solid prosthetic implants for orthopaedic, craniofacial and dental applications. Excluding failures attributable to implant micromotion and infection, lack of optimal osteointegration along solid prosthetic implants may be due to inadequate consideration of the geometric configuration of the implant surface.

Thus, the importance of geometry of an implant for bone repair and replacement may not be limited to the internal porous configuration (as in the case of porous biomaterial implants) but also to the external design of solid prostheses to be used for orthopaedic and dental applications.

The present invention is the innovative application of the results of the inventor's research and experimentation into the importance of the geometric configuration of a material for use in bone repair and replacement, in the form of a manufactured article having a unique outer implant surface, and in the form of a biomaterial having both a unique implant surface and a unique porous configuration, for use in particular embodiments of the article, and that is capable of inducing the spontaneous initiation of bone formation even if not in direct contact with viable bone.

According to the invention, broadly, there is provided a bone implant for implanting into a subject at a site where bone growth is required, said implant comprising a body with an outer surface which defines dents which are selected, according to their shape and dimensions, for their ability to induce or to enhance the rate and/or amount of bone growth at the site.

The dents may be in the form of concavities having a diameter in the region of about 200 $\mu$m to about 3000 $\mu$m, more preferably 1600 $\mu$m, and with a depth in the region of about 200 $\mu$m to about 3000 $\mu$m, more preferably about 800 $\mu$m.

In the following disclosures, it will become apparent that the osteoinductive geometric configuration can be imparted to a porous biomaterial implant for applications in bone repair (i.e., by fabricating a porous biomaterial with specific geometry of the porous spaces within and on the outer surface of the implant) as well as solid prosthetic implants in which the specific geometric configurations are imparted only to the external surface of the implant. By virtue of the preparation of osteoinductive geometric configurations, both biomaterial implants are endowed with intrinsic osteoinductive activity.

For the purpose of the porous biomaterial implant with osteoinductive geometric configuration, according to the invention, there is provided a method of preparing a biomaterial which can be used for at least part of a bone implant to be implanted into a patient at a site where bone growth is required, which method includes preparing the biomaterial of a sintered ceramic with an interconnected porous configuration which includes concavities having such shapes and dimensions as impart to the biomaterial the ability to induce or enhance the rate and/or amount of bone growth at the site.

The biomaterial may be made by a range of ceramic processing techniques including, but not limited to a fugitive phase method or by a sponge impregnation method.

If the fugitive phase method is used, then it involves selecting or manufacturing stearic acid beads of a suitable size, mixing a ceramic powder with the stearic acid beads, compacting the resulting mixture to form a compact, and sintering the compact.

A typical fugitive phase method for making the biomaterial of the invention is the following.

Stearic acid is obtained from SMM Chemicals under product number 8224 land stearic acid beads are manufactured to approximately the required size, typically 1–2 mm diameter. The yield is then sieved to obtain a narrow distribution around the required size. Hydroxyapatite powder obtained from Merck S. A under product number 2196 and the classified stearic acid beads are mixed by tumbling without additives in a proportion of 70% beads by mass. The resulting dry mixture is loaded into a press mould, sealed , and cold isostatically pressed at a pressure of 200 MPa. The green compact thus produced is machined if necessary. The green compact is placed on platinum foil and sintered according to the following program:

| Segment | 1 | 2 | 3 | 4 | 5 |
|---|---|---|---|---|---|
| Temperature (° C.) | 25 | 300 | 1200 | 1200 | 25 |
| Time (hrs) | 0 | 6 | 6 | 1 | 6 |

If the sponge impregnation method is used then it involves attaching a layer of synthetic hydroxyapatite to the surfaces of a polyurethane foam material having continuous and interconnecting pores. This impregnated foam is then thermally treated to form a reticulated ceramic with three-dimensional continuous pores. More particularly this method includes (a) selecting an organic resin with a three-dimensional network structure which is a negative replica of the desired configuration of the biomaterial, (b) impregnating a slurry of a ceramic into the organic resin, (c) drying the slurry, and (d) removing the organic resin.

The porous sintered hydroxyapatite artefact fabricated using either of the methods described above will consist of a framework of hydroxyapatite delineating porous spaces formed by the coalescence of repetitive sequence of concavities.

The irregular spheroid shape of the resin and their interconnections provide a three dimensional foamy-like network, and the resulting hydroxyapatite artefact defines porous spaces having a plurality of concavities often separated by convexities, ie the hydroxyapatite is a replica of the organic resin. Variable dimensions of the concavities which make the porous spaces after sintering the hydroxyapatite slurry can be obtained by using polyurethane foams of different dimensions increasing or decreasing the dimensions of the starting resin material, it is possible to obtain porous spaces made of larger or smaller concavities when sintering the hydroxyapatite slurry.

The optimum dimensions of the concavities imparting the specific osteoinductive geometric configuration to the porous biomaterial as determined by the inventors, is as follows:

The inner geometry of the biomaterial is characterised by pores which are substantially spherical in shape and in the region of 300 $\mu$m to 3000 $\mu$m in diameter, preferably about 1600 $\mu$m.

It is important to point out that the substantial spheroidal shape of the porous spaces is due to the apposition, within the inner part of the porous biomaterial, of single concavities specifically fabricated by both fugitive and impregnation methods described above.

The specific geometric configuration of the biomaterial is also imparted at the outer surface of the porous biomaterial.

Thus, at the outer surface of the biomaterial, the osteoinductive geometric configurations are concavities with a maximum diameter in the region of about 200 µm to about 3000µm, more preferably 1600 µm, and with a maximum depth in the region of about 200 µm to about 3000 µm, more preferably about 800 µm.

Thus according to the invention there is provided a biomaterial implant for bone repair which is capable of spontaneous induction of bone both within the inner porous spaces, and the concavities prepared on the outer surface of the biomaterial implant. The ability to induce bone formation in the concavities of the outer surface is advantageous, since this will enhance the rate of osteointegration with the surrounding viable bone when implanted into a patient at a site where bone growth is required.

The invention extends to a method of inducing and enhancing the rate and amount of bone growth in a patient, in a site where bone growth is desired, which includes selecting a porous biomaterial implant having an appropriate overall shape and size for accommodation at the site of a bone defect, and comprising a porous framework, preferably of sintered hydroxyapatite, within porous spaces and outer surface concavities having a diameter of about 200 µm to about 3000 µm and a depth of about 200 µm to about 1600 µm, and placing the porous biomaterial implant in the patient at the site of a bone defect where bone formation and growth is required.

Where the porous biomaterial implant is made of sintered hydroxyapatite, the method may include treating the outer and inner surfaces of the porous implant with etchants, and may further include adsorbing bone morphogenetic proteins onto the porous spaces of the implant, before placing the implant in the site where bone growth is required. In this case, there is potentiation of the bone inductive activity by the exogenous application of BMPs.

A preferred method of treating the biomaterial is to wet the sintered hydroxyapatite of which it is made, by pipetting suitable amounts of 5 mM hydrochloric acid (preferably about 300 µl per 1000 µg of sintered hydroxyapatite) onto and into the hydroxyapatite substratum. In this case the biomaterial of the invention not only induces but also enhances the rate and amount of bone formation and growth.

For the purpose of the solid implant with osteoinductive geometric configurations for dental, craniofacial and orthopaedic applications, according to the invention, there is provided a solid implant for implantation into a patient at a site where bone replacement is required, said implant comprising a body with an outer surface with specific geometric configurations, which are selected, according to their ability to induce the spontaneous initiation of bone and to enhance the rate and the amount of bone at the site of implantation.

The optimum geometric configuration of the outer surface of the solid implant as determined by the inventors is as follows:

At the outer surface of the solid biomaterial implant, the preferred geometric configuration are concavities with a maximum diameter in the region of about 200 µm to about 3000 µm, more preferably 1600 µm, and with a maximum depth in the region of about 200 µm to about 3000 µm more preferably about 800 µm. The regions of the outer surfaces at the respective peripheries of the concavities, may be rounded, and in a preferred embodiment of the biomaterial according to the invention, the outer surface generally does not have any sharp edges and the indentations are spaced apart from one another by a distance of about 500 µm to about 3000 µm preferably about 2000 µm.

The invention extends to a method of inducing or enhancing the rate and/or amount of bone growth in a patient, in a site where bone replacement is desired, which includes selecting a solid implant having an appropriate overall shape and size for accommodation in the site, and comprising a body with an outer surface which defines concavities having a diameter of about 200 µm to about 3000 µm and a depth of about 200 µm to about 1600 µm and placing the implant in the patient in the site where bone replacement and growth is required.

In a preferred embodiment of an implant according to the invention, the solid implant is preferably of sintered hydroxyapatite or other ceramics such as zirconia and alumina.

According to the invention there is provided a solid implant made of sintered hydroxyapatite with specific geometric configuration which are selected, according to their shape and dimensions, for their ability to induce the spontaneous initiation of bone and to enhance the rate and/or amount of bone at the site of implantation into a patient.

The manufacture of solid implants of hydroxyapatite with specific concavities prepared on the outer surface involves mixing of ceramic powder (such as hydroxyapatite) with binder, pressing the compacts using a die and pistons with specific concavities and sintering the said compacts.

A typical process includes the following:

Polyethylene glycol 1000 binder, (Merck product number 807488), is added at 15% by mass to hydroxyapatite powder by dissolving the binder in ethanol, adding the hydroxyapatite and subsequently evaporating the ethanol whilst mixing.

The powder is pressed at a pressure of 5–20 MPa in a die between two pistons, lubricated with a solution of stearic acid in ethanol. Damage of the compact during separation from the pistons was minimised by placing double sheets of thin polyethylene sheets between the powder and pistons before pressing. The pistons contain hemispherical protrusions of 1000 µm and 2000 µm diameter, respectively, produced by drilling holes and brazing 1000 µm and 2000 µm diameter steel spheres to a depth of 1 radius in the flat piston surfaces. Compacts of hydroxyapatites of any shape with concavities on the other surface of 1000 µm and 2000 µm respectively, are thus produced on the flat surfaces. The green compacts are then placed on platinum foil covered and sintered.

If the hydroxyapatite used for the preparation of the compacts is hydroxyapatite powder from Merck S. A. (product number 2196) then compact are sintered according to the following program:

| Segment | 1 | 2 | 3 | 4 | 5 |
|---|---|---|---|---|---|
| Temperature (° C.) | 50 | 400 | 1150 | 1150 | 20 |
| Time (hrs) | 1 | 10 | 4 | 1 | 4 |

Furthermore, the solid implant of sintered hydroxyapatite may have BMPs adsorbed thereon, to further potentiate and/or accelerate induction of bone formation.

Whilst a preferred method for preparing such solid implants, as described above for dental and orthopaedic applications is using sintered hydroxyapatite or other ceramics such as zirconia and alumina, it is also possible to prepare according to the invention solid implants made of metals (preferably bio-tolerant such as titanium).

In such cases of solid implants made of titanium or other bio-tolerant metals, the implant has an outer coating of an additional biomaterial over the outer surface concavities as described above. The biomaterial may be hydroxyapatite, or such other biomaterial as may aid osteointegration of the implant in use. Such a coating will be bio-active, e.g. hydroxyapatite (or derivatives such as fluoroapatite), BIOGLASS®, CERAVITAL®; bio-inert, e.g. alumina, silicon nitride, pyrolytic carbon; bio-tolerant, e.g. polytetrafluoroethylene (PTFE), polymethyl methacrylate (PMMA), or bio-resorbable, e.g. polyglycolic acid (DEXON S®), 90% polyglycolic acid/polylactic acid (VICRYL®), poly(hydroxybutyrate)poly)hydroxyvalerate) (PHB-PHV), tricalcium phosphate. Typically, a calcium phosphate ceramic, such as hydroxyapatite is applied to the outer surface of the implant body. The thickness of the coating applied to the outer body of the solid implant may be in the region of about 50 μm to about 400 μm or more, preferably in the region of 60 μm to 120 μm.

Furthermore, the coating, preferably of hydroxyapatite, may have BMPs adsorbed therein, to further potentiate and/or accelerate induction of bone formation.

Further, according to the invention, there is provided a method of manufacturing an implant for bone replacement, which method includes providing a body of a suitable material, preferably hydroxyapatite or other ceramics, and size for implanting into a patient at a site where bone replacement and growth is required, and providing in the outer surface of the body, concavities which are of a shape and dimensions which induce or enhance the rate and/or amount of bone growth at the implantation site.

In such cases of solid implants made of metal such as titanium, then the method includes coating the implant with a biomaterial which will aid osteointegration. Such material is preferably bioactive, such as hydroxyapatite.

Manufacture of the implant may include profiling by either
(a) non-contact machining, such as laser machining, spark eroding, or
(b) contact machining via mechanical means, such as turning, drilling, milling, grinding, etc. For example, in dentistry, a pure titanium or titanium alloy rod of suitable starting diameter can be turned down on a lathe to an appropriate diameter for implantation (usually either in the mandible or maxilla). Subsequently, the concavities in the outer surface can be provided by machining.

If the implant, when of metal, is to be used uncoated then, after machining, standard surface preparation techniques can be carried out, e.g. degreasing, cleaning, passivating, and sterilising. Surface preparations such as grit blasting prior to implantation and before cleaning can also be performed.

For applying a coating of a biomaterial to the implant, when made of metal such as titanium, to aid osteointegration, a number of physical and chemical techniques are available. These include, but are not limited to:
1. Biological deposition from simulated body fluid.
2. Adhesively bonding hydroxyapatite (HA) to the substrate.
3. Radiofrequency sputtering.
4. Pulsed laser deposition.
5. Hot isostatic pressing (HIPPING).
6. Reactive physical vapour deposition.
7. Slurry coating.
8. Electrophoretic deposition and sintering.
9. High velocity flame spraying.
10. Ion beam sputter deposition.
11. Magnetron sputtering.

Furthermore, after coating, a number of post-treatments can be carried out, for example,
1. Radiofrequency glow discharge treatment.
2. Vacuum heat treatment.
3. Ion implantation.

The currently preferred deposition techniques are based on thermal spray technology and, in particular, vacuum plasma spraying and air plasma spraying.

The invention is now described by way of the following non-limiting examples and with reference to the accompanying photographs and drawings, from which it will become apparent that the specific geometric configuration imparts to both porous and solid biomaterials the ability to induce the spontaneous initiation of bone formation.

Figure 2:
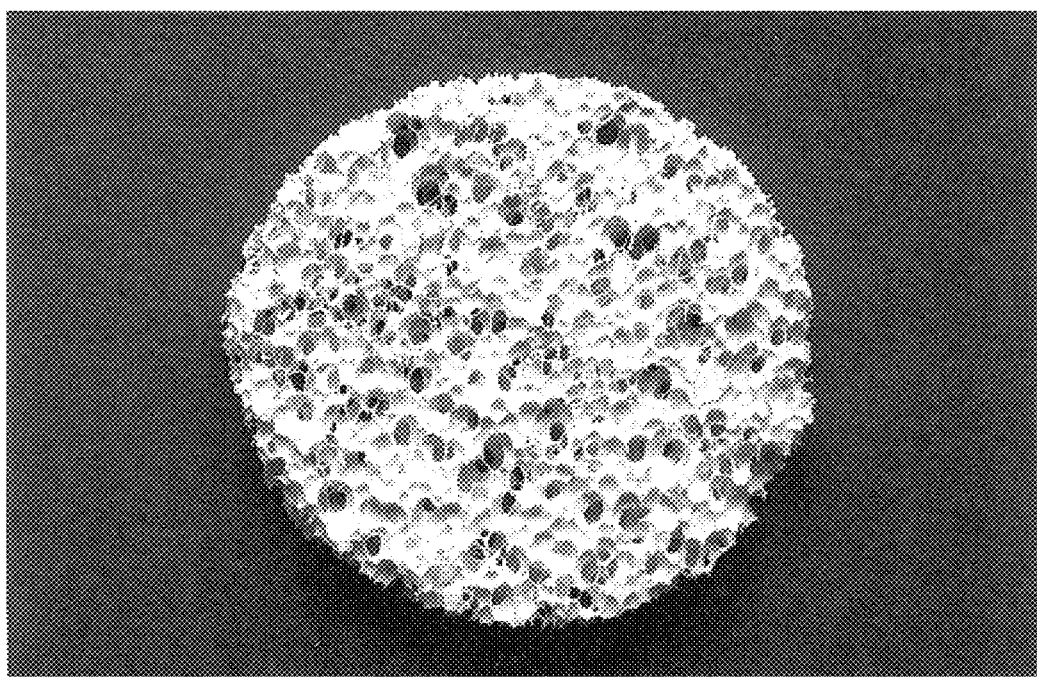

In the Examples:

EXAMPLE 1 describes the spontaneous induction of bone within the porous spaces of the porous hydroxyapatite implant having specific geometric configurations, after implantation in extraskeletal sites of a primate;

EXAMPLE 2 describes bone formation and growth into the porous hydroxyapatite implant having specific geometric configurations, after implantation in skeletal sites of a primate;

EXAMPLE 3 describes the rapid induction of bone formation within the porous spaces of the porous hydroxyapatite implant having specific geometric configurations, after implantation in extraskeletal sites of a primate after adsorption of BMPs onto the hydroxyapatite;

EXAMPLE 4 describes the rapid induction of bone formation and growth into the porous hydroxyapatite implant having specific geometric configurations, after implantation in skeletal sites of a primate after adsorption of BMPs onto the hydroxyapatite;

EXAMPLE 5 describes the spontaneous induction of bone only in specific geometric configurations created on the external surface of a solid implant of sintered hydroxyapatite when implanted in extraskeletal sites of a primate;

EXAMPLE 6 describes the osteointegration, bone formation and growth, and bone interlocking along the geometric configuration of a solid implant of titanium coated with hydroxyapatite and implanted in the edentulous jaw of a primate, and it extends also to describe the influence of the geometric configuration on cell attachment and tissue matrix deposition in the specific geometric configurations created on the outer surface of the solid implant of titanium coated with hydroxyapatite when implanted in contact with muscular tissue of a primate;

In the photographs and drawings:

FIGS. 1 and 2 are photomacrographs of the porous sintered hydroxyapatite before implantation in a primate; and in particular, FIG. 1 is a photomacrograph of the sintered porous hydroxyapatite prepared in disc configuration, suitable for implantation in circular calvarial defects of the baboon, with osteoinductive geometric configuration which form the framework of the hydroxyapatite, and FIG. 2 is a scanning electron micrograph of the sintered porous hydroxyapatite illustrating the repetitive sequence of concavities according to the present invention.

Figure 3:
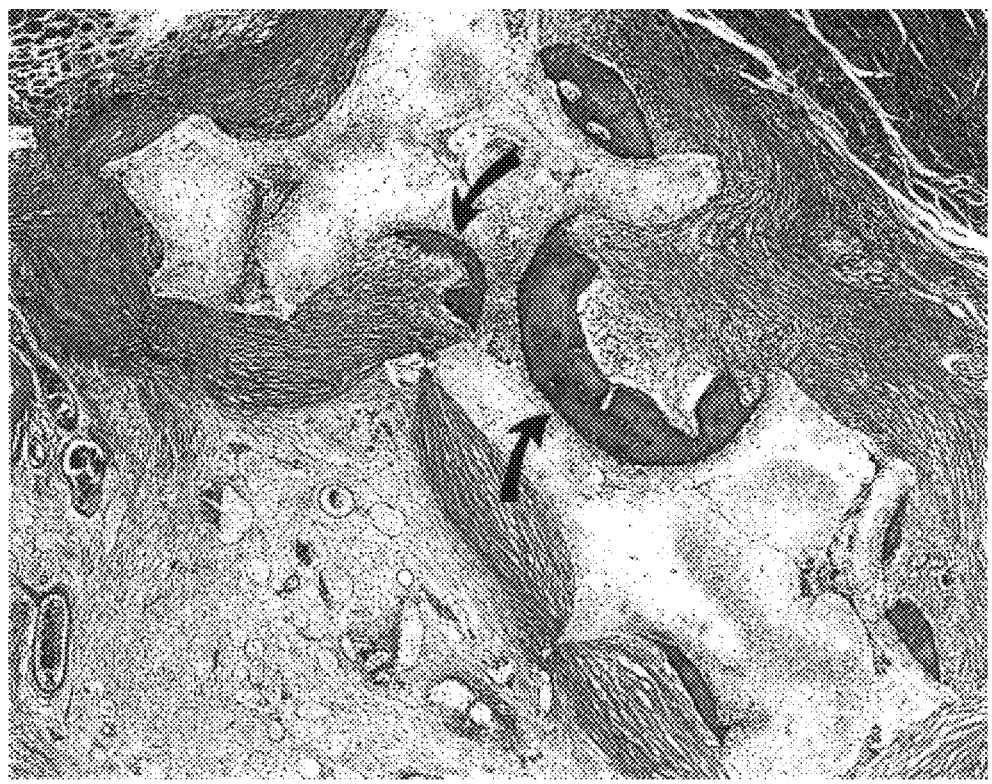
Figure 4:
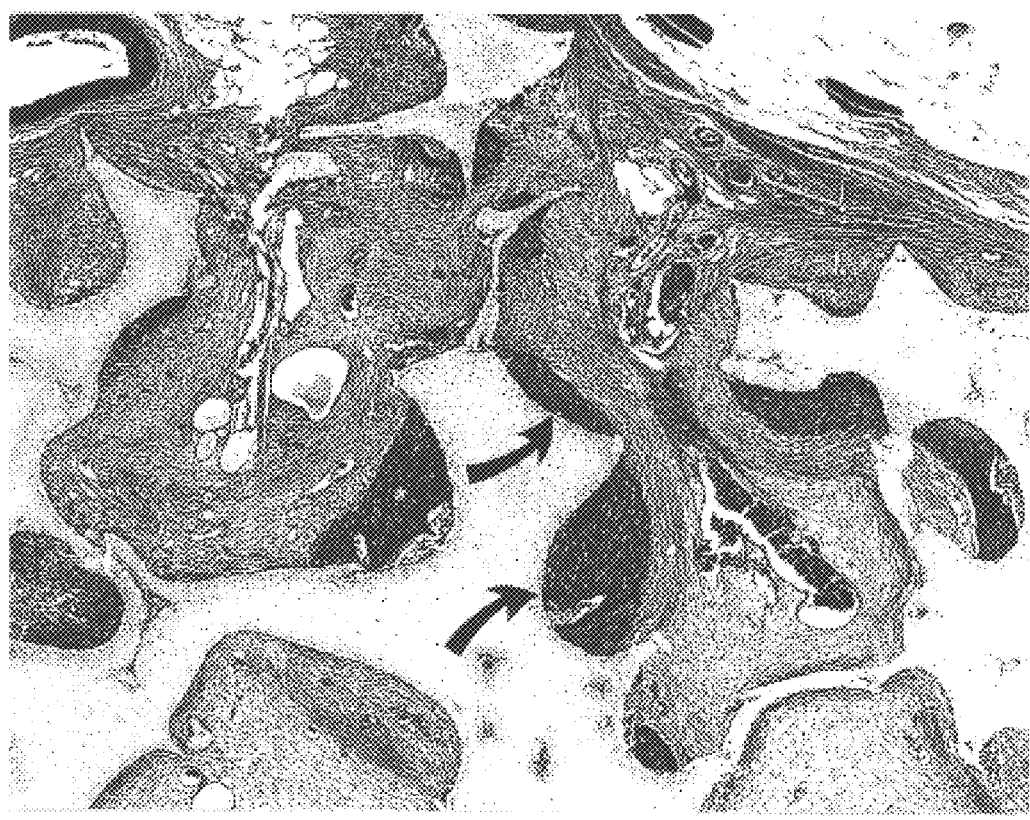
Figure 5:
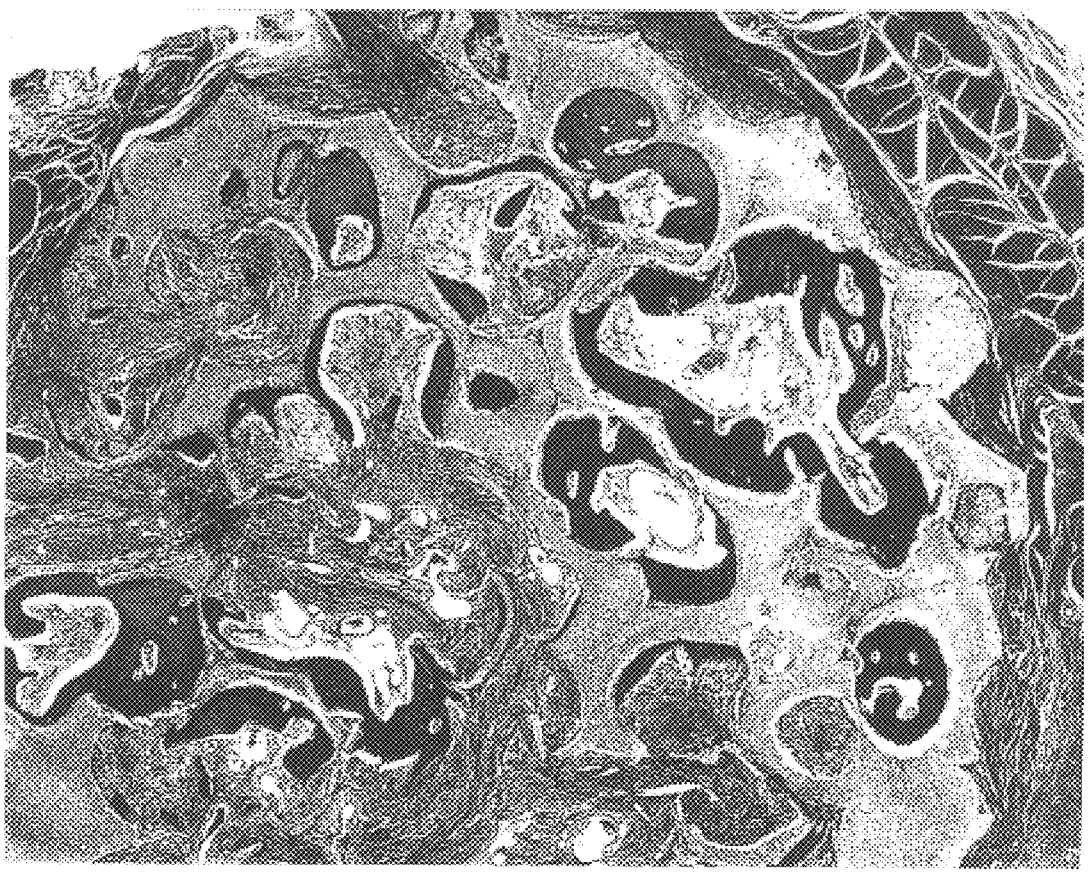
Figure 6:
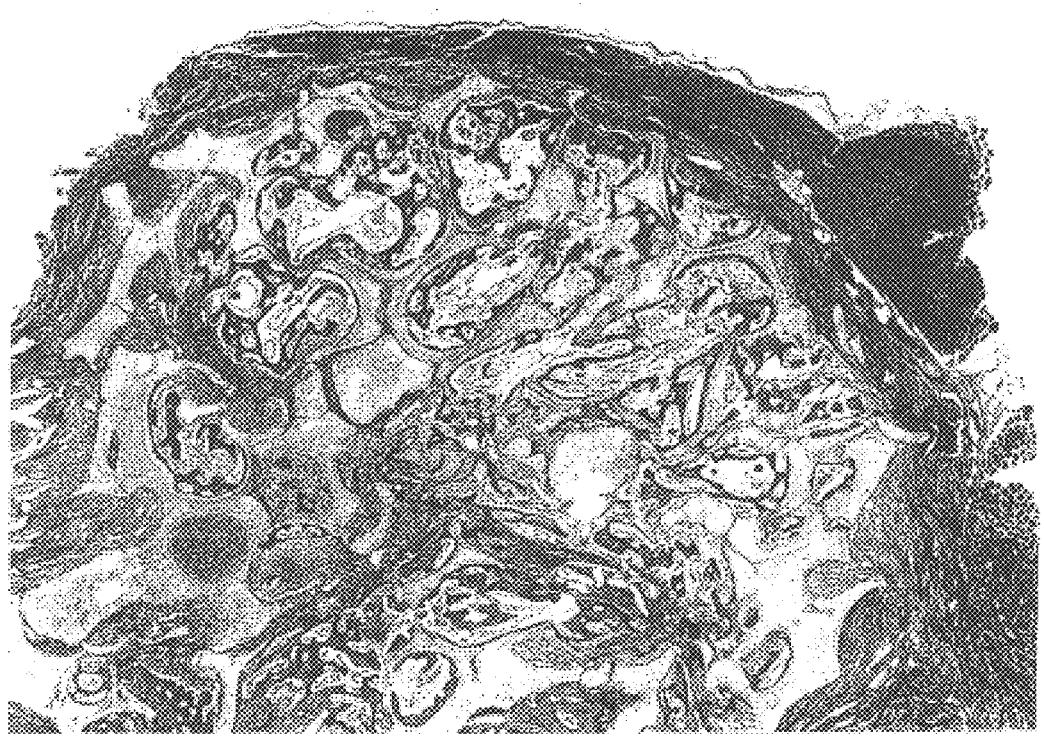

FIGS. 3 to 6 are photomicrographs of sections prepared from sintered porous hydroxyapatite rods according to the invention, harvested from extraskeletal intramuscular sites (rectus abdominis) of a primate; in particular, FIG. 3 shows a photomicrograph of histological section prepared from specimen of sintered porous hydroxyapatite rods harvested from intramuscular sites of the baboon on day 90 after implantation: bone (arrows) had spontaneously formed only along concavities of the hydroxyapatite substratum; FIG. 4 shows a photomicrograph of histological section prepared from specimen of sintered porous hydroxyapatite rods harvested from intramuscular sites of the baboon on day 90 after implantation: bone (arrows) had spontaneously formed only along concavities of the hydroxyapatite substratum; FIG. 5 shows an extensive induction of bone after pretreatment of the sintered porous hydroxyapatite with 5 mM hydrochloric acid; and FIG. 6 shows a photomicrograph of a histological section prepared from a specimen of sintered porous hydroxyapatite in rod configuration pre-treated with BMPs and harvested from intramuscular sites of the baboon on day 30 after implantation: extensive bone induction and generation of bone marrow within the spheroidal porous spaces.

Figure 7:
Figure 8:
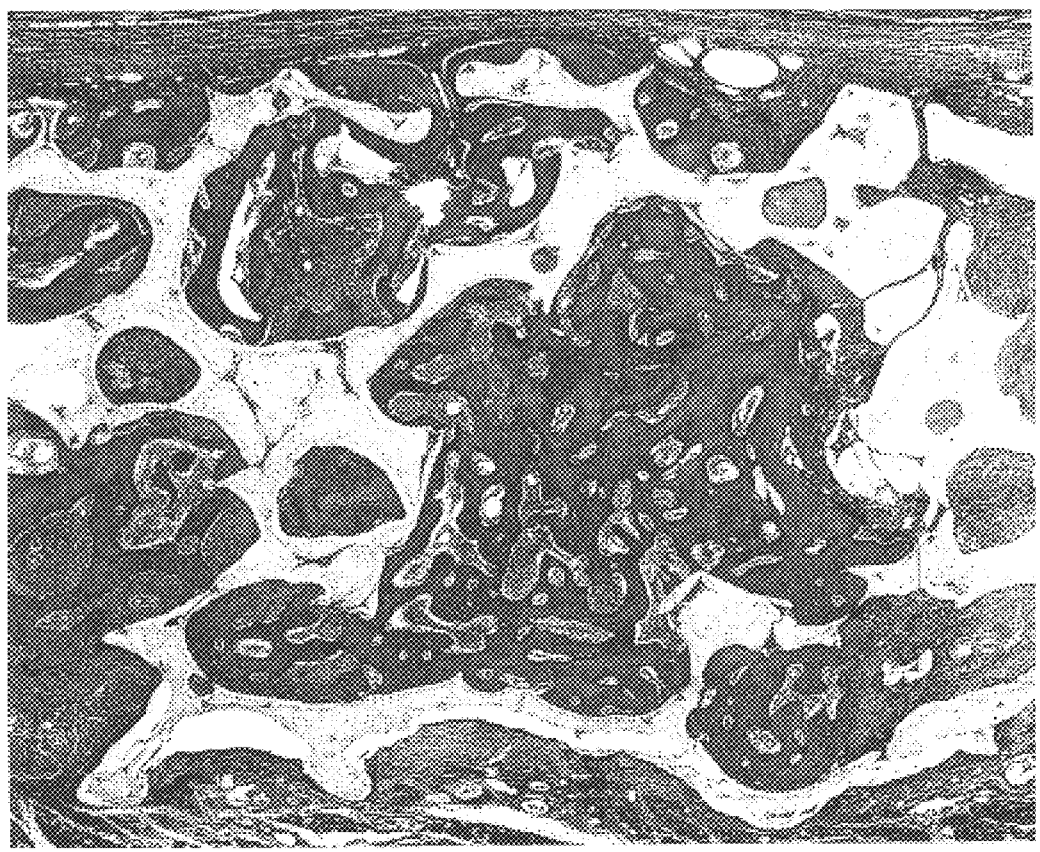
Figure 9:

FIGS. 7 to 9 are photomicrographs of sections prepared from sintered porous hydroxyapatite discs according to the invention, harvested from the calvaria of a primate; in particular, FIG. 7 shows a complete bone growth and penetration in the porous spaces of a sintered porous hydroxyapatite disc implanted in the calvaria of an adult baboon and harvested on day 90 after surgery. Arrows indicate the margins of the surgically created defects; FIG. 8 shows a higher magnification showing bone growth within the spheroidal porous spaces (now occupied by newly formed bone) of the sintered hydroxyapatite implanted in the calvaria of an adult baboon and harvested on day 90 after surgery; and FIG. 9 shows a photomicrograph of a histological section prepared from a specimen of sintered porous hydroxyapatite in disc configuration pre-treated with BMPs and harvested from the calvaria of the baboon on day 30 after implantation: extensive bone induction within the porous spaces of the sintered hydroxyapatite.

Figure 10:
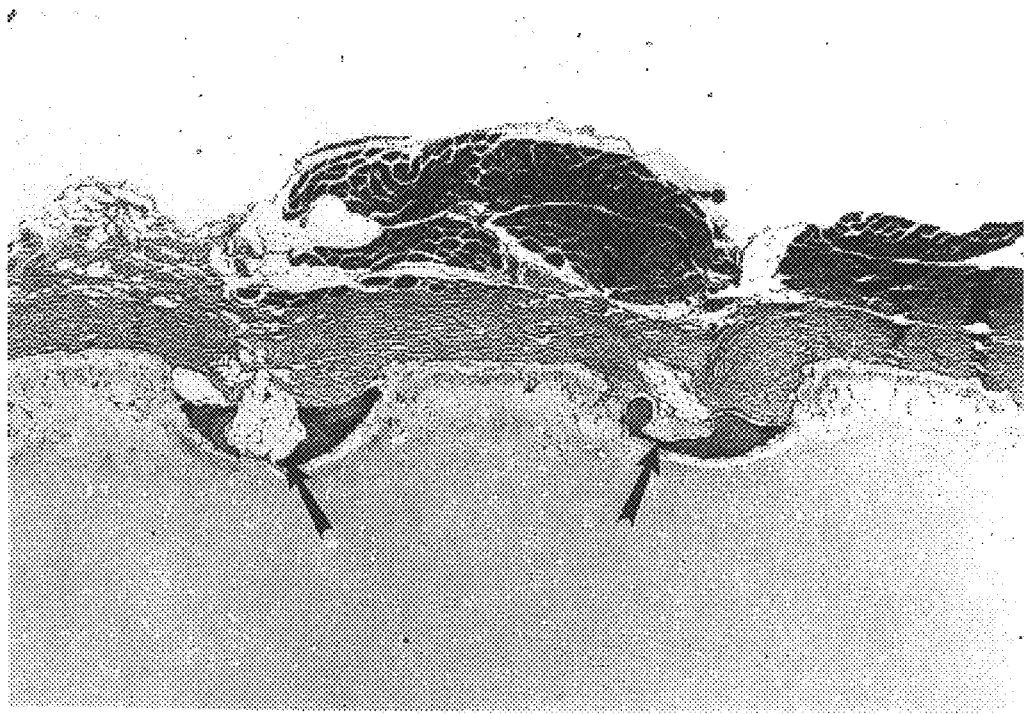
Figure 11:
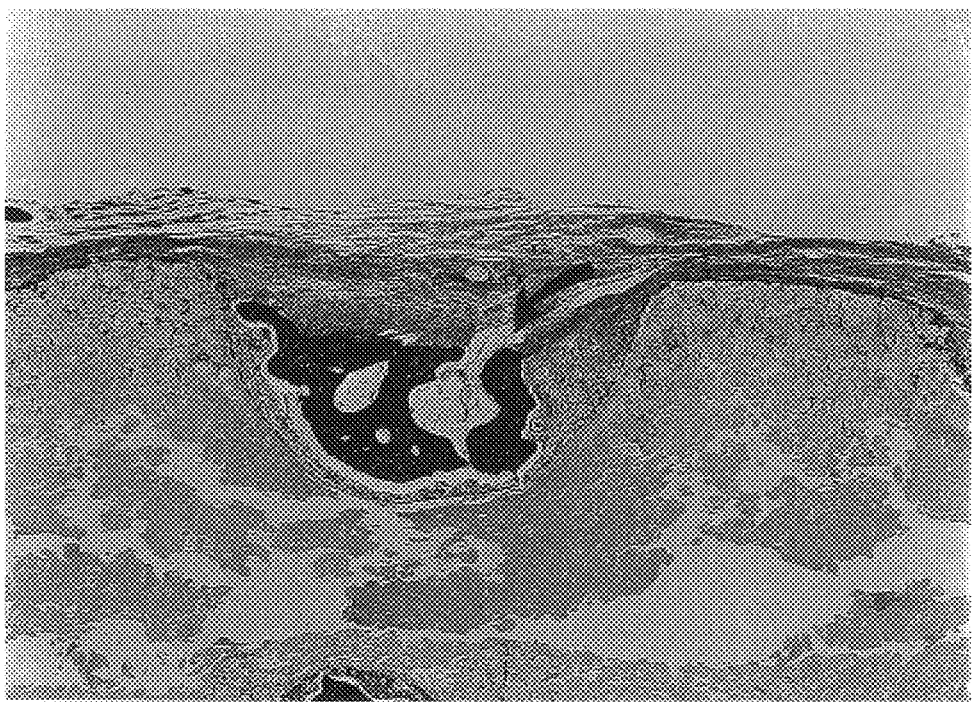

FIGS. 10 and 11 are photomicrographs of sections prepared from solid implants made of sintered hydroxyapatite with specific geometric configurations according to the invention; in particular, FIG. 10 shows a photomicrograph of histological section prepared from specimen, of solid implants of sintered hydroxyapatite with osteoinductive geometric configurations of the present invention. Extensive bone formation and remodelling with generation of bone marrow (arrows) only in the concavities prepared on the outer surface of the solid hydroxyapatite. The specimens were harvested on day 90 after implantation in the rectus abdominis of an adult baboon; and FIG. 11 shows photomicrograph of histological section prepared from specimen of solid implants of sintered hydroxyapatite with osteoinductive geometric configurations of the present invention. Extensive bone formation and remodelling with generation of bone marrow (arrows) only in the concavities prepared on the outer surface of the solid hydroxyapatite. The specimens were harvested on day 90 after implantation in the rectus abdominis of an adult baboon.

Figure 12:
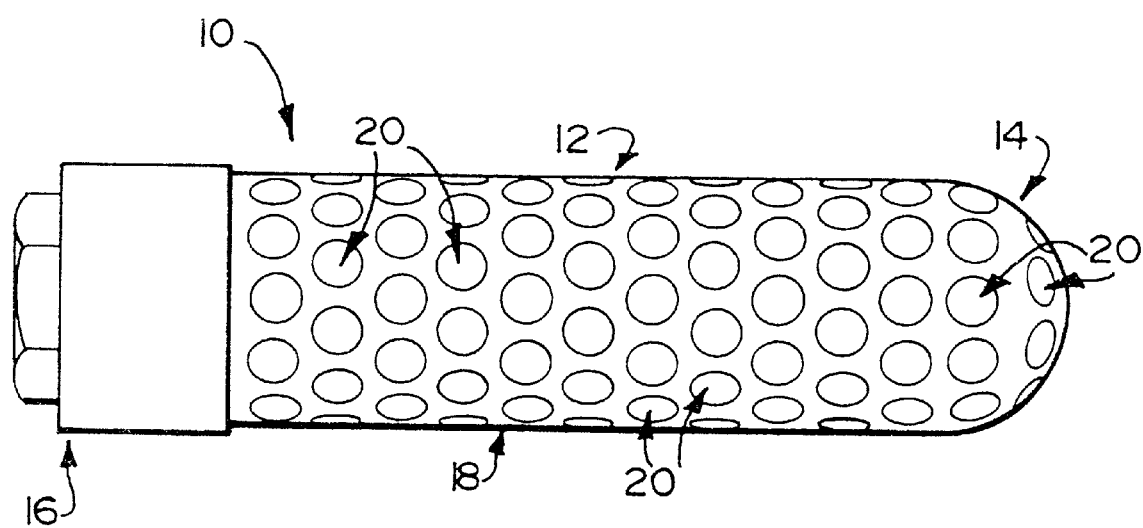
Figure 13:
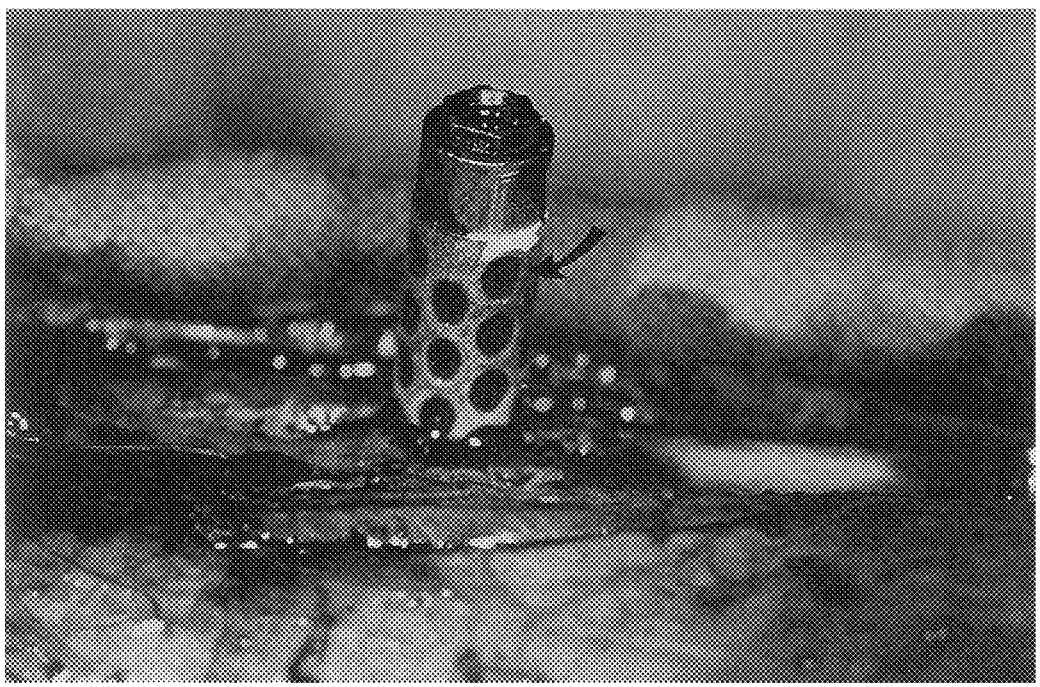

FIG. 12 schematically illustrates a typical solid implant according to the invention;

FIG. 13 illustrates a solid implant similar to that of FIG. 12, made of titanium with hydroxyapatite coating (e.g. a dental implant) and geometric configurations at the outer surface according to the invention, just prior to implantation into a bony site of the primate; it shows a clinical photograph of the dental implant of the present invention just before surgical insertion in osseous site of the baboon; the arrows indicate blood that has filled the concavities prepared on the outer surface of the implant.

Figure 14:
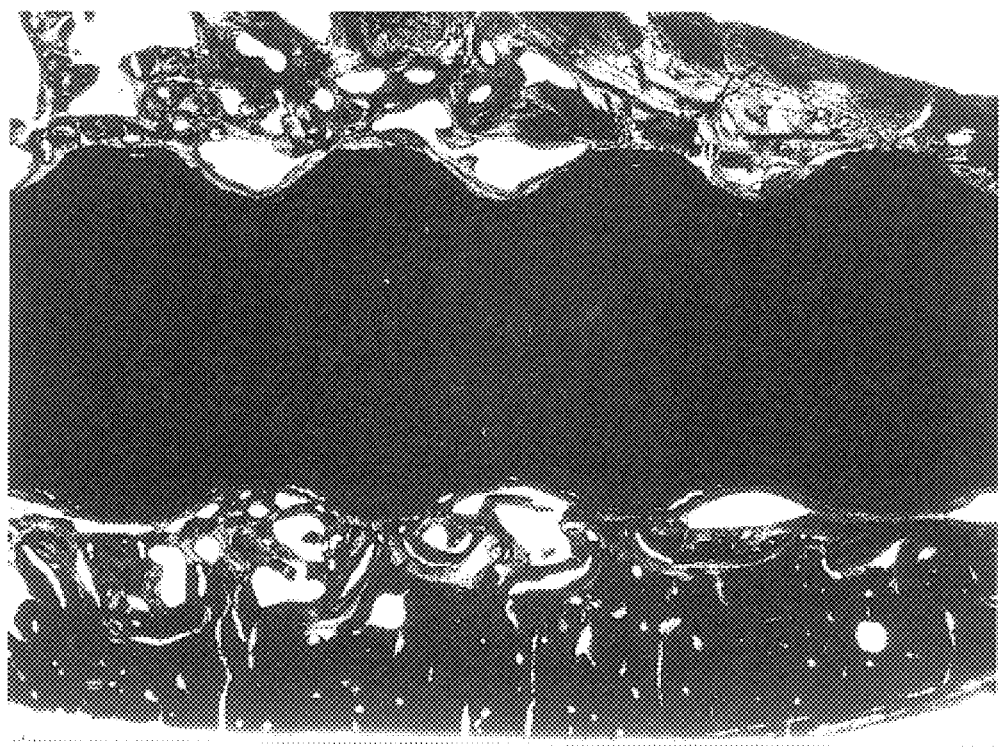
Figure 15:
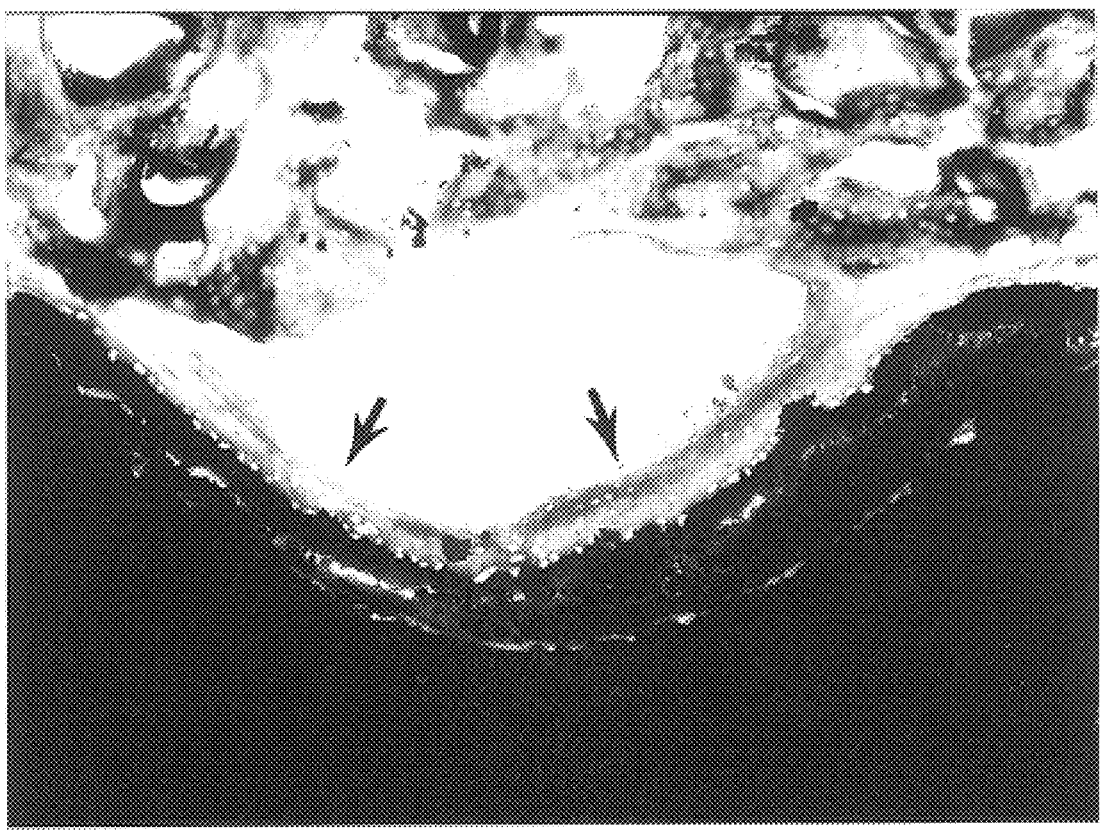
Figure 16:
Figure 17:
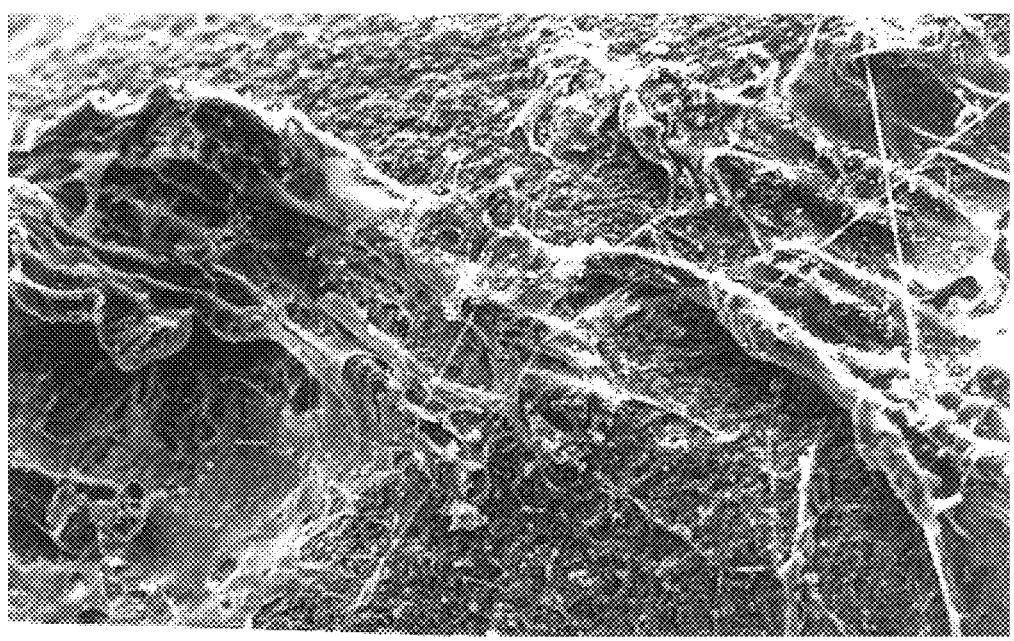
Figure 18:
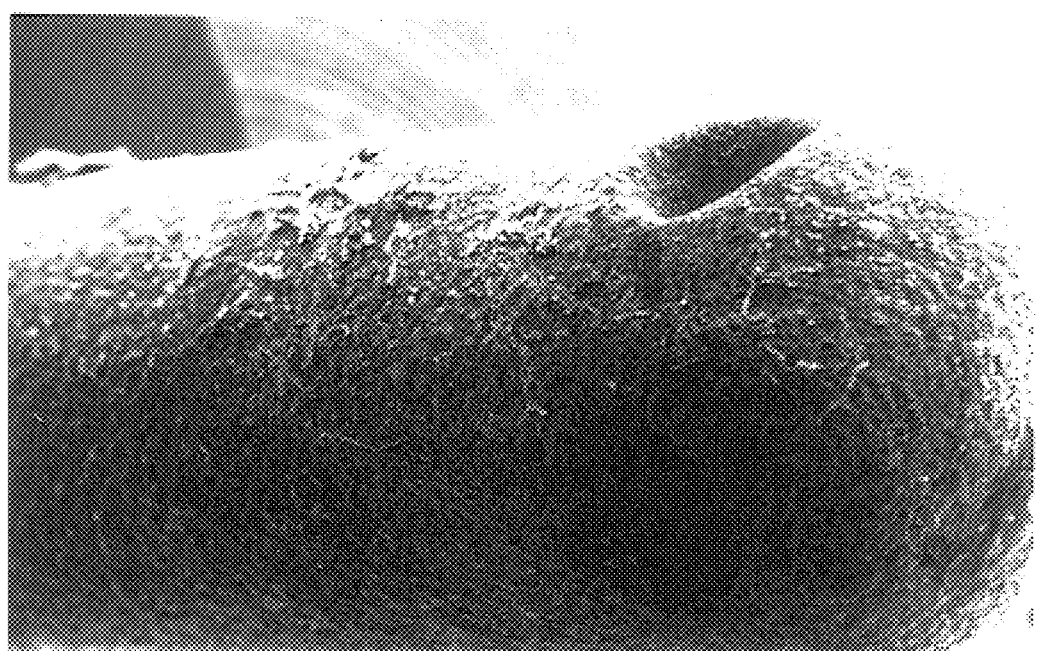

FIGS. 14 and 15 are photomicrographs of sections prepared from solid implants made of titanium with hydroxyapatite coating and geometric configurations at the outer surface according to the invention and harvested from the jaw of a primate; FIG. 14 is a photomicrograph of a histological section prepared from a dental implant prepared according to the invention and harvested on day 90 after surgical insertion in the jaw of the baboon. Bone formation and growth, and bone interlocking had formed along the concavities prepared on the outer surface of the solid implant; and FIG. 15 is a higher magnification of previous section (FIG. 14) highlighting bone formation and growth in direct apposition with the hydroxyapatite coating plasma sprayed over titanium (arrows). There was generation of bone marrow between the bone in contact with the implant and the surrounding bone of the jaw, but this cannot be seen in FIG. 15; and FIGS. 16 to 18 are photomacrographs of solid implants made of titanium coated with hydroxyapatite according to the invention illustrating preferential cell attachment and tissue matrix deposition within the specific geometric configuration of the implant when compared with standard implants without preparation of concavities at the outer surface of the implant; in particular, FIG. 16 shows a scanning electron micrograph of the dental implant of the present invention showing cell attachment and tissue matrix deposition preferentially within the concavities prepared at the outer surface of the implant; FIG. 17 shows a scanning electron micrographs of the dental implant of the present invention showing cell attachment and tissue matrix deposition preferentially within the concavities prepared at the outer surface of the implant; and FIG. 18 is a scanning electron micrograph of a standard dental implant without concavities on the outer surface of the implant showing lack of cell attachment and tissue matrix deposition.

The sintered porous hydroxyapatite biomaterial according to the invention was prepared in the following manner.

A slurry of well dispersed hydroxyapatite powder obtained from Merck S. A. under Product number 2196, was prepared in an alcohol/binder/plasticizer solution and a polyurethane foam was impregnated with this slurry. The composition of the binder/plasticizer mix was as follows: 90 g polyethylene glycol #6000; 150 g poly-vinyl butyral; 240 g ethanol absolute; 600 g trichloroethylene. The slurry was prepared using the following batch composition: 70 g hydroxyapatite; 50 g ethanol absolute; 1 g emphos PS-21A deflocculant; 36 g binder/plasticizer mix. A commercial low porosity, low density polyurethane foam #30/14 (density/hardness) was used.

The foam was first immersed into the slurry and repeatedly compressed and expanded to ensure complete coverage of all pore walls. The excess slurry was then removed and the coated foam allowed to dry. The ceramic atefact was formed by heating the impregnated foam in stages to ensure the complete burn-out of all organic matter and finally sintering the hydroxyapatite using the following firing schedule: 90° C./h to 250° C., hold for 2 hours; 50° C./h to 650° C., hold for 5 hours; 200° C./h to 1200° C., holding for 2 hours; cooling at 200° C./h to ambient.

The artificial implants were shaped into discs and rods for implantation in the primate, but it should be understood that the implants can be of any other configuration with different dimensions for the required implant to fit the damaged or missing region of the bone.

The rods measured 20 mm in length and 7 mm in diameter and the discs measured 25 mm in diameter and 4 mm in thickness, and the pore sizes were in the region of 300 $\mu$m to 2200 $\mu$m.

Example 1

To investigate the intrinsic osteoinductive activity of the sintered porous hydroxyapatite of the present invention, the rods were implanted intramuscularly (rectus abdominis) of primates (baboon, *Papio ursinus*) since only the extraskeletal implantation permits the histological investigation of bone formation by induction, avoiding the possible ambiguities of intraskeletal sites (where bone growth occurs from the vehicle bone interfaces of a bone defect). Before implantation, some of the rods were treated, just before implantation, with a liquid vehicle consisting of 5 mM hydrochloric acid. This treatment was achieved by wetting the sintered porous hydroxyapatite rods by pipetting 5 mM hydrochloric acid onto and into the hydroxyapatite substratum (preferably 300 $\mu$l per 1000 $\mu$g of sintered hydroxyapatite).

Example 2

To investigate the overall effect of the sintered hydroxyapatite as biomaterial for bone repair and replacement, the discs were implanted in non-healing cranial defects, 25 mm in diameter, surgically prepared in the calvaria of adult baboons.

Examples 3 and 4

To investigate the efficacy of the sintered porous hydroxyapatite as carrier and delivery system for growth and morphogenetic factors, some implants were pre-treated by adsorbing BMPs, solubilized in 5 mM hydrochloric acid, onto the hydroxyapatite in both rod and disc configuration, which were then implanted in the rectus abdominis and the calvaria of the baboon, respectively.

Example 5

To investigate the intrinsic osteoinductive activity of the solid implants for bone replacement of the present invention, sintered solid implants of hydroxyapatite in disc configuration (20 mm in diameter and 4 mm in thickness) with concavities prepared on the outer surface of the discs according to the invention, were implanted intramuscularly (rectus abdominis) of the baboon.

The rods, which were implanted intramuscularly, were harvested on day 30 and 90 respectively after implantation. The discs of sintered porous hydroxyapatite were also harvested on day 30 and 90 after implantation. Rods and discs with surrounding muscular tissue and calvaria bone, respectively, were processed for histological analysis, and serial histological sections were prepared and stained using conventional methods.

The discs of solid sintered hydroxyapatite, which were implanted intramuscularly, were harvested on day 30 and 90 respectively after after implantation, and processed for histological analysis using conventional methods.

Intramuscular implants (rods):

The results shows that spontaneous bone formation occurred by day 30 and 90 after intramuscular implantation. Photomicrographs (as shown in FIGS. 3, 4 and 5) were taken from sections prepared from the sintered hydroxyapatite rods harvested from the intramuscular sites (rectus abdominis) of the baboon 90 days after implantation. The arrows in FIGS. 3 and 4 indicate bone which formed spontaneously along concavities of the hydroxyapatite substratum. FIG. 5 shows extensive bone induction and generation of bone marrow after pre-treatment of the sintered porous hydroxyapatite with 5 mM hydrochloric acid.

FIG. 6 shows the rapid and extensive bone induction and generation of bone marrow as early as 30 days after intramuscular implantation after adsorption of BMPs onto the hydroxyapatite.

From these photomicrographs it is evident that the bone formation occurred consistently in concavities of the porous surfaces of the sintered hydroxyapatite implant, but did not form on convexities, which observation supports the view that the geometric configuration of the implant is of critical importance for spontaneous bone induction to occur.

Moreover, enhanced osteoinduction is obtained by pre-treatment of the implants just before implantation by a liquid vehicle comprising 5 mM hydrochloric acid as shown in FIG. 5.

It is important to note that this was achieved in the primate, and in a body site not in contact with viable bone, and underscores the critical importance of the geometry of the hydroxyapatite substratum for the spontaneous induction of bone formation.

Furthermore, rapid bone induction can be achieved (as shown in FIG. 6) by prior adsorption of BMPs onto the hydroxyapatite, which observation indicates that the sintered porous hydroxyapatite implant of the present invention is efficaceous as carrier and as delivery system for the osteogenic activity of exogenous BMPs previously adsorbed onto the hydroxyapatite.

Calvarial implants (disc):

The results showed complete incorporation of the porous sintered hydroxyapatite implant within the cranial defects 90 days after implantaation. Photomicrographs (see FIGS. 7 and 8) were taken from sections prepared from sintered porous hydroxyapatite discs harvested from the calvaria of the adult baboon, 90 days after surgery. The arrows in FIG. 7 indicate the margins of the surgically created calvarial defects. FIG. 8 is a higher magnification showing bone formation and growth within the spheroidal porous spaces (now occupied by newly formed bone) of the sintered porous hydroxyapatite.

Adsorption of BMPs onto the hydroxyapatite discs prior to insertion into calvarial defects of adult baboons showed extensive bone formation as early as 30 days after surgery, as shown in FIG. 9.

Intramuscular implants (solid discs):

The results showed that spontaneous bone formation occurred by day 30 and 90 after intramuscular implantation of the solid hydroxyapatite implants of the present invention. FIGS. 10 and 11 show bone formation and generation of bone marrow (arrows) only within the concavities of solid hydroxyapatite discs harvested from intramuscular sites of the baboon on day 90 after implantation.

From these photomicrographs it is evident that the spontaneous induction of bone formation occurred only in the concavities prepared on the outer surface of the solid sintered hydroxyapatite implant, which observation indicates that the geometric configuration of the solid implant is also of critical importance for bone induction to occur, and that solid implants with an outer surface of hydroxyapatite with specific geometric configuration are endowed with intrinsic osteoinductive activity.

In FIG. 12, reference numeral 10 generally indicates a solid implant according to the invention which comprises a body 12 manufactured from the following material: Ti-6Al-4V. The body comprises a rod of circular section with a diameter of 3.85 mm, having a rounded head 14 at its forward end and integral formations 16 at its back end which formations 16 facilitate location of the implant body 12 in a desired site in a subject. The implant body 12 has an outer surface 18 which defines a plurality of concavities 20, each having a maximum diameter of about 1600 μm, and a maximum depth of about 800 μm. The concavities 20 are spaced apart a distance of about 800 μm.

FIG. 13 is a second embodiment of an implant according to the invention (just before surgical implantation into a primate), which is similar in almost all respects to the implant 10 (as shown in FIG. 12). The only difference is that the embodiment of FIG. 13 is a plasma sprayed hydroxyapatite-coated implant. The coating thickness is in the region of about 60 μm to about 80 μm. Optionally bone morphogenetic proteins (BMPs) can be adsorbed onto the hydroxyapatite, thereby to achieve more rapid osteointegration by providing additional osteoinduction by exogenous applications of native or recombinant human BMPs.

The coating of hydroxyapatite was applied to the implant body 12 by air plasma spraying the hydroxyapatite coating (high crystallinity, low porosity, highly adherent) to the suitable prepared (see above) titanium substrate using conventional deposition techniques. A Metco 9MB plasma spray gun operating with an Ar/H$_2$ plasma at 35 kW was used to deposit the coating. Prior to spraying with the hydroxyapatite (powder supplied by Metco-Plasma Technik, product AMDRY 6020), the titanium substrate was prepared for coating, i.e. roughened by grit blasting with alumina grit to produce the following surface profile:

$R_a$>3 μm, $R_t$>20 μm, $R_z$>15 μm.

Typical spray parameters are given below:

| Plasma Gas | |
|---|---|
| Primary | Argon (5 bar) |
| Secondary | Hydrogen (5 bar) |
| Gun Power | 25–35 kW |
| Powder Feed Rate | 10–30 g/min |
| Stand-Off Distance | 60–100 mm |
| Gun Velocity | 100 mm/min |

Example 6

To investigate the overall effect and efficacy of the solid implant of the present invention as biomaterial implant for bone replacement, solid implants of titanium with hydroxyapatite coating and with concavities prepared at the outer surface of the solid implant, were implanted in the edentulous jaw of the baboon.

The solid implants of titanium with hydroxyapatite coating, which were implanted in the edentulous jaw of the baboon, were harvested on day 30 and 90 after surgical implantation.

The results showed that bone formation and growth had occurred along the concavities of the solid implant of titanium coated with hydroxyapatite of the present invention (as shown in FIG. 14). FIG. 15 is a high power view showing bone formation and growth in direct apposition to the hydroxyapatite plasma sprayed onto the titanium in the region of a concavity prepared on the outer surface of the solid implant (arrows). Bone formation and growth within the concavities enhances bone interlocking with the implant and superior fixation of the implant with surrounding viable bone, advantageous for implants for bone replacement during function.

FIGS. 16 and 17 are photomacrographs showing cell attachment and tissue matrix deposition preferentially occurring within the concavities prepared on the outer surface of the implant, which observation indicates the importance of the geometric configuration on tissue differentiation and tissue matrix deposition when compared to standard implants without the preparation of concavities, as shown in FIG. 18.

It should be understood that although the abovementioned example of an implant according to the invention is one which is particularly suitable for dental applications, the invention should not be construed as being limited to dental implants. Indeed, application of the invention extends to craniofacial and orthopaedic use, as solid prosthetic implants for bone replacement (e.g. femoral and knee prostheses as in orthopaedic practice).

A major advantage of the invention, at least as exemplified, is the capability of the inventive implant with specific geometry to induce bone formation even in cases where the implant is not placed in direct contact with viable bone. It is of great importance to note that the invention provides biomaterial implants for orthopaedic, craniofacial and dental applications that are capable of spontaneous bone induction when implanted into the baboon, a primate that has bone physiology and remodelling comparable to man [9], the ultimate recipient of the biomaterial implant of the present invention.

Accordingly this invention provides a biomaterial for bone repair and replacement which is capable of spontaneous initiation of bone formation, i.e. a biomaterial implant with intrinsic osteogenic activity. It also provides sintered porous ceramic biomaterials and methods for their manufacture derived from synthetic hydroxyapatite particle as a starting material, capable of both osteoconduction and osteoinduction when implanted into a bone defect. Further, the invention provides sintered porous ceramic biomaterials for bone replacement having a defined porous macrostructure and a defined geometric configuration of the porous structure. Still further, the invention provides porous sintered ceramic biomaterials which provide an optimal substratum for adsorption of growth and morphogenetic factors, including, but not limited to, BMPs.

The sintered hydroxyapatite of the present invention has the following advantages over the hydroxyapatite derived via hydrothermal exchange from naturally occurring coral. The sintered hydroxyapatite of the invention (a) is pure highly crystalline hydroxyapatite, (b) the pore sizes and uniformity thereof in an implant comprising such pure hydroxyapatite, is controllable, and (c) the shapes of the pores are beneficially more rounded, being substantially spherical in configuration. In contrast, the hydroxyapatite derived from the naturally occurring coral material (a) is not pure hydroxyapatite (generally comprising about 10% of a phosphate impurity), (b) does not have controllable pore sizes, and (c) comprises pores in the form of channels which extend along substantially the entire width or length of an implant made from the conventional material. Furthermore, the osteoinductive geometric configuration prepared on the outer surface of the implant of both porous and solid implants of sintered hydroxyapatite has the advantage of initiating the spontaneous induction of bone formation along the concavities on the outer surface of the implant, thereby enhancing the osteointegration with the surrounding viable bone, when the implant is placed into a bone defect of the primate. It is important to point out that, in coral-derived hydroxyapatite, bone is never observed on the outer surface of the implant [5, 7].

It will therefore be appreciated that a major advantage of the invention, at least as exemplified, is the capability of the inventive implant with specific geometry to induce bone formation even in cases where the implant is not placed in direct contact with viable bone. Another advantage of the invention is that porous hydroxyapatite obtained after sintering is an optimum substratum for adsorption of BMPs additionally potentiating the osteogenic properties of the implant.

The preferred method of complexing growth and morphogenetic factors onto the porous substratum of the sintered hydroxyapatite biomaterial of the invention, is as follows:
(a) the biomaterial is placed in a chromatography column,
(b) the BMPs are dissolved or suspended in a suitable fluid vehicle therefor,
(c) the dissolved or suspended BMPs are introduced into the column at a controlled rate, and
(d) the BMPs are contacted with the biomaterial of the invention in the column so that the BMPs are adsorbed onto the biomaterial.

Details of such a method of adsorption are available from South Africa Patent No. 92/3608.

Instead, BMPs can be manually loaded onto the sintered hydroxyapatite biomaterial according to the invention, by means of a pipette containing the BMPs dissolved or suspended in a suitable fluid vehicle therefor preferably 5 mM hydrochloric acid.

FIGURE LEGENDS

FIG. 1:
Photomacrograph of the sintered porous hydroxyapatite prepared in disc configuration, suitable for implantation in circular calvarial defects of the baboon, with osteoinductive geometric configuration which form the framework of the hydroxyapatite.

FIG. 2:
Scanning electron micrograph of the sintered porous hydroxyapatite illustrating the repetitive sequence of concavities according to the present invention.

FIGS. 3 and 4:
Photomicrographs of histological sections prepared from specimens of sintered porous hydroxyapatite rods harvested from intramuscular sites of the baboon on day 90 after implantation: bone (arrows) had spontaneously formed only along concavities of the hydroxyapatite substratum.

FIG. 5:
Extensive induction of bone after pre-treatment of the sintered porous hydroxyapatite with 5 mM hydrochloric acid.

FIG. 6:
Photomicrograph of a histological section prepared from a specimen of sintered porous hydroxyapatite in rod configuration pre-treated with BMPs and harvested from intramuscular sites of the baboon on day 30 after implantation: extensive bone induction and generation of bone marrow within the spheroidal porous spaces.

FIG. 7:
Complete bone growth and penetration in the porous spaces of a sintered porous hydroxyapatite disc implanted in the calvaria of an adult baboon and harvested on day 90 after surgery. Arrows indicate the margins of the surgically created defects.

FIG. 8:
Higher magnification showing bone growth within the spheroidal porous spaces (now occupied by newly formed bone) of the sintered hydroxyapatite implanted in the calvaria of an adult baboon and harvested on day 90 after surgery.

FIG. 9:
Photomicrograph of a histological section prepared from a specimen of sintered porous hydroxyapatite in disc configuration pre-treated with BMPs and harvested from the calvaria of the baboon on day 30 after implantation: extensive bone induction within the porous spaces of the sintered hydroxyapatite.

FIGS. 10 and 11:
Photomicrographs of histological sections prepared from specimens of solid implants of sintered hydroxyapatite with osteoinductive geometric configurations of the present invention. Extensive bone formation and remodelling with generation of bone marrow (arrows) only in the concavities prepared on the outer space of the solid hydroxyapatite. The specimens were harvested on day 90 after implantation in the rectus abdominis of an adult baboon.

FIG. 12:
Schematic illustration of a solid implant with specific geometric configurations according to the invention.

FIG. 13:
Clinical photograph of the dental implant of the present invention just before surgical insertion in osseous site of the baboon. Arrows indicate blood that has filled the concavities prepared on the outer surface of the implant.

FIG. 14:
Photomicrograph of a histological section prepared from a dental implant prepared according to the invention and harvested on day 90 after surgical insertion in the jaw of the baboon. Bone formation and growth, and bone interlocking had formed along the concavities prepared on the outer surface of the solid implant.

FIG. 15:
Higher magnification of previous section (FIG. 14) highlighting bone formation and growth in direct apposition with the hydroxyapatite coating plasma sprayed over titanium (arrows). There was generation of bone marrow between the bone in contact with the implant and the surrounding bone of the jaw, but this cannot be seen in FIG. 15.

FIGS. 16 and 17:
Scanning electron micrographs of the dental implant of the present invention showing cell attachment and tissue matrix deposition preferentially within the concavities prepared at the outer surface of the implant.

FIG. 18:
Scanning electron micrograph of a standard dental implant without concavities on the outer surface of the implant showing lack of cell attachment and tissue matrix deposition.

REFERENCES

1. Wells JW (1956) Scleractinia. In: Moore RC (ed) Treatise on Invertebrate Paleontology. University of Kansas Press, Kansas City, pp. 328–444.
2. Weber JN, White EW (1973) Carbonate minerals as precursors of new ceramics, metal, and polymer materials for biomedical applications. Miner Sci Engng 5:151–165.
3. Roy, DM, Linnehan SK (1974) Hydroxyapatite formed from coral skeletal carbonate by hydrothermal exchange. Nature 247:220–222.
4. White EW, Weber JN, Roy DM, Owen EL (1975) Replamineform porous biomaterials for hard tissue implant applications. J Biomed Mater Res Symposium 6:23–27.

5. Ripamonti U. The morphogenesis of bone in replicas of porous hydroxyapatite obtained from conversion of calcium carbonate exoskeletons of coral. J Bone Joint Surg [Am] 1991; 73: 692–703.
6. Ripamonti U, Ma S, Reddi AH. The critical role of geometry of porous hydroxyapatite delivery system in induction of bone by osteogenin, a bone morphogenetic protein. Matrix 1992; 12: 202–212.
7. Ripamonti U, van den Heever B, van Wyk J. Expression of the osteogenic phenotype in porous hydroxyapatite implanted extraskeletally in baboons. Matrix 1993; 13: 491–502.
8. Van Eeden S, Ripamonti U. Bone differentiation in porous hydroxyapatite is regulated by the geometry of the substratum: implications for reconstructive craniofacial surgery. Plast Reconstr Surg 1994; 93: 959–966.
9. Schnitzler Cm, Ripamonti U, Mesquita JM. Histomorphometry of iliac crest trabecular bone in adult male baboons in captivity. Calcif Tiss Int 1993; 52: 447–454.

What is claimed is:

1. A bone implant for implanting into a subject at a site where bone growth is required, the implant comprising a body of sintered bioactive ceramic biomaterial, the body having intrinsic osteoinductive activity and having a network of interconnected coalesced rounded inner porous spaces as well as surface concavities of the body interconnected with the porous spaces, wherein the rounded inner porous spaces consist essentially of substantially spherical or spheroidal shaped spaces having diameter of between 300 $\mu$m and 3000 $\mu$m.

2. A bone implant according to claim 1, wherein the surface concavities consist essentially of concavities having a diameter of about 200 $\mu$m to 3000 $\mu$m, and a depth of 200 $\mu$m to 3000 $\mu$m, thereby enhancing the intrinsic osteoinductive activity of the body.

3. A bone implant according to claim 1, wherein the biomaterial is sintered hydroxyapatite, and has native or recombinant human bone morphogenetic proteins adsorbed therein.

4. A bone implant according to claim 1, wherein the outer surface of the body has been treated with a liquid etchant.

5. A method of inducing or enhancing the rate and/or amount of bone growth in a subject, in a site where bone growth is desired, which method includes:

selecting a bone implant according to claim 1, and having an appropriate overall shape and size for accommodation in the site; and placing the implant into the subject in the site where bone growth is desired.

6. A bone implant according to claim 1, wherein the biomaterial has native or recombinant bone morphogenic proteins adsorbed therein.

7. A bone implant according to claim 1, wherein the biomaterial is sintered hydroxyapatite.

* * * * *